(12) United States Patent (10) Patent No.: US 8,064,661 B2
Komori et al. (45) Date of Patent: Nov. 22, 2011

(54) CELL CULTURE DEVICE, IMAGE PROCESSING DEVICE AND CELL DETECTING SYSTEM

(75) Inventors: Yoshihiro Komori, Chiba (JP); Tsutomu Suzuki, Chiba (JP)

(73) Assignee: Kaneka Corporation, Osaka (JP)

( * ) Notice: Subject to any disclaimer, the term of this patent is extended or adjusted under 35 U.S.C. 154(b) by 734 days.

(21) Appl. No.: 11/718,807

(22) PCT Filed: Nov. 9, 2005

(86) PCT No.: PCT/JP2005/020529
§ 371 (c)(1),
(2), (4) Date: Apr. 25, 2008

(87) PCT Pub. No.: WO2006/051813
PCT Pub. Date: May 18, 2006

(65) Prior Publication Data
US 2008/0273786 A1 Nov. 6, 2008

(30) Foreign Application Priority Data
Nov. 9, 2004 (JP) .................................. 2004-324456

(51) Int. Cl.
*G06K 9/00* (2006.01)
(52) U.S. Cl. ........................................ 382/128; 128/922
(58) Field of Classification Search .................. 382/100, 382/128, 129, 130, 131, 132; 128/922; 378/4–27
See application file for complete search history.

(56) References Cited

U.S. PATENT DOCUMENTS
2003/0103662 A1* 6/2003 Finkbeiner .................... 382/128

FOREIGN PATENT DOCUMENTS

| | | |
|---|---|---|
| EP | 0 099 229 A2 | 1/1984 |
| JP | 2000-275539 | 10/2000 |
| JP | 2000-316120 A | 11/2000 |
| JP | 2001-275659 | 10/2001 |
| JP | 2002-312761 | 10/2002 |
| JP | 2003-021628 | 1/2003 |
| JP | 2003-235540 | 8/2003 |
| JP | 2004-271337 | 9/2004 |
| JP | 2004-532410 A | 10/2004 |
| JP | 2005-192485 | 7/2005 |
| WO | WO 94/17493 A1 | 8/1994 |
| WO | WO 99/67739 A1 | 12/1999 |
| WO | WO 02/086498 A1 | 10/2002 |

OTHER PUBLICATIONS

Extended European Search Report, dated Nov. 3, 2010, issued in corresponding European Patent Application No. 05806165.6.

* cited by examiner

*Primary Examiner* — Anand Bhatnagar
(74) *Attorney, Agent, or Firm* — Antonelli, Terry, Stout & Kraus, LLP.

(57) ABSTRACT

In a container of a cell culture device, a light source and a camera are arranged on both sides of an incubator, and the camera or incubator can be moved in relation to each other.
An image of cells in the incubator is captured with a given focus.
The medium, image density, and noise component of images captured while varying the focus of the camera have substantially similar pixel values.
Consequently, by subjecting the data on the images captured with such different focuses to differential processing, only the cell portion can be extracted without being influenced by the color variation of the medium, the variation of the amount of light, the difference in brightness between the central and peripheral areas of the image, and the noise.

7 Claims, 7 Drawing Sheets

(BOTTOM SURFACE OF THE INCUBATOR IS THE FOCAL POINT)

SHIFTING DISTANCE OF THE CAMERA

FOCAL POINT (BOTTOM SURFACE OF THE INCUBATOR)

FOCAL POINT (FRONT)

FOCAL POINT (BACK)

AFTER DIFFERENCE CALCULATION PROCESS

CELL CULTURE DEVICE, IMAGE PROCESSING DEVICE AND CELL DETECTING SYSTEM

TECHNICAL FIELD

The present invention relates to a cell culture device, image processing device and cell detecting system capable of extracting a cell portion from a plurality of image data obtained during the cell culture process.

BACKGROUND ART

In the process of cell culture, image observation of a culture state of microscopic cells has been carried out in the past mainly in laboratories of organization such as universities and institutes, by taking out the petri dish in which the culture is placed from a thermostatic chamber and observing the cells using a microscope.

Also, in order to extract the cells from image data obtained during cell culture, the threshold value has been calculated based on distribution of pixel values, and pixels equal to the threshold value and above or below have been extracted as the cell. However, the method using the above-mentioned threshold processing had a problem that the image turned out whitish, whereby detecting as if more cells exist than the actual amount. Consequently, in order to stably extract the cells without being influenced by color variation of the medium, light volume variation of the light source, difference in brightness between the central and peripheral areas of the image and the noise in the image, it has been fundamental to carry out a filtering process such as denoising, smoothing filter or edge enhancement.

In Patent Document 1, a method is described which monitors brightness variation in image data, generate a trigger signal at a specific threshold value, take images repeatedly with a camera, and obtains the added and averaged value of the images.

Patent Document 1: JP-A-2000-275539

Also, a technique for enabling observation of a motion state of individual cells by arranging a light source and a CCD camera facing each other placing an incubator therebetween, and imaging the cells in the incubator at an early stage of culture using the CCD camera is described in Non-patent Document 1.

Non-patent Document 1: Journal of Bioscience and Bioengineering Vo. 94, no. 4,351-356.2002 "Characterization of Cellular Motion Through Direct Observation of Individual Cells at Early Stage in Anchorage-Dependent Culture".

DISCLOSURE OF THE INVENTION

Problems to be Solved

In a conventional method for observing the cells in culture process by taking them out of the thermostatic chamber and observing them using a microscope, since the cells are exposed to the atmosphere in the laboratory, there has been a problem of having difficulty continuing the culture again after observing the cells with the microscope.

A conceivable means to solve the problem would be to incorporate the microscope into the incubator, but it would create another problem i.e. the increase in size and cost.

Also, a conventional method of carrying out the filtering process has been influencing the accuracy of cell-extraction through the filtering process to be executed before the cell-extraction process. The problems such as the difference in brightness between the central and peripheral areas or noise included in the image can be eliminated to some extent by this filtering process, and the technique described in Patent Document 1 can also have the effect of eliminating noise included in the image to some extent. However, depending on image data, there have been cases that the above-mentioned effectiveness was limited or the outline of the cells was indistinct.

Also, the technique described in the above-mentioned non-patent document 1 is for simply imaging the cells in the incubator, and the respective cells are individually identifiable at early stage in culturing, but it becomes harder to individually identify them as the culturing process progresses.

The present invention paid-attention to the above-mentioned problems, and the objective is to provide a cell culture device capable of observing the progress of cell culture without taking the cells out of the device.

Also, the present invention is for providing a cell culture device, image processing device and cell detecting system capable of extracting the cells in images without being influenced by color variation of the medium, difference in brightness between the central and the peripheral areas of the image, and the noise.

Means to Solve the Problems

A cell culture device related to the present invention is characterized in having a container capable of forming a space sealed off from the outer atmosphere, having arranged in the container an incubator for culturing cells, a light source for irradiating light to the cells in culture process in the incubator, and image acquiring device placed in the back of the incubator with respect to the light source and is for imaging the cells in the culture process, as well as comprising means for creating image data for extracting the cells by processing the acquired image using the image acquiring means.

Also, the present invention is characterized in comprising:

incubator means for culturing the cells;

image acquiring means for acquiring images of the cells from the incubator means;

focal position adjusting means for moving either the image acquiring means or the incubator means, and adjusting a focal point of the image acquiring means to be set in front and back of the cells in culture process in the incubator; and extracting means for extracting only the cell portions, with respect to the plurality of focal points set by the focal point position adjusting means, by subjecting the plural pieces of image data each having a different focal point acquired by the image acquiring process to differential processing, and performing a binarization processing on the images subjected with differential processing.

Such configuration makes it possible to move the camera being a means to obtain images or the incubator in relation to each other, and to acquire images at arbitrary focal points. And the plural pieces of images imaged by changing the focal point of the camera have the pixel values with substantially the same medium and noise element. Therefore, through subjecting a plurality of image data imaged with different focal points to differential processing, influence by color variation of the medium, variation of the light volume, difference in brightness between the central and the peripheral areas of the image or noise are eliminated, and only the cell part can be extracted.

Furthermore, the cell culture device related to the present invention comprises focal point position calculating means for calculating the focal point of the image acquiring means in order to acquire the most suitable image for extracting only the cell part using the extracting means.

This means calculates the focal point position where the outline of the cells becomes clear or the position of image acquiring means with respect to the acquired image using methods such as profiling, Fourier transformation and differentiation. The image obtained at the calculated focal point becomes a suitable image for the cell extracting process. And by carrying out the positioning of image acquiring means to the calculated focal point position upon the next measurement time, the focus can be taken consistently with the same accuracy.

The cell culture device related to the present invention comprises position-compensating means for compensating the position of a plurality of image data acquired by the image acquiring means.

By this means the deterioration of accuracy for extracting the cells due to displacement of the plurality of images can be prevented, by compensating the displacement in X/Y-directions and rotation direction of images caused upon changing the focus.

An image-processing device relating to the present invention comprises:

image acquiring means for acquiring images of the objects being scattered on a plane surface and having a predetermined range of thickness;

focal point position adjusting means for adjusting a focal point of the image acquiring means to be positioned in front and back of thickness direction of the object; and extracting means for extracting only an object, in the plurality of focal point positions set by the focal point position adjusting means, by subjecting the plurality of image data having different focal point positions acquired by the image acquiring means to differential processing.

With such configuration, it is possible to extract only the cell portions without being influenced by color variation of the medium, variation of the light volume, difference in brightness between the central and peripheral areas of the image or noise, by subjecting the plurality of image data imaged with different focal points using image processing means to differential processing.

A cell extracting system relating to the present invention comprises:

image acquiring means for acquiring images of the cells scattered on a plane surface;

focal point position adjusting means for adjusting the focal point of the image acquiring means to the upper and lower portion in the orthogonal direction of the plane surface on which the cells are scattered; and extracting means for extracting only the cell portions, in a plurality of focal point positions set by the focal point position adjusting means, by subjecting the plurality of image data having different focal point positions acquired by the image acquiring means to differential processing.

With such configuration, it is possible to extract only the cell portions without being influenced by color variation of the medium, variation of light volume, difference in brightness between the central and peripheral areas of the image or noise, by subjecting the plurality of image data imaged with different focal points using image processing means to differential processing.

Effect of the Invention

According to the present invention, observation of the cells in culture process can be carried out without taking them out of the device, thus fungi other than culture target would not be mixed into the incubator.

Also, according to the present invention, it is possible to extract only the cell portions without being influenced by color variation of the medium, variation of light volume, difference in brightness between the central and peripheral areas of the image or noise.

BRIEF DESCRIPTION OF THE DIAGRAMS

DESCRIPTION OF THE SYMBOLS

11 . . . cell culture device, 12 . . . incubator, 13 . . . CCD camera, 14 . . . image-processing unit, 15 . . . converter, 16 . . . camera/incubator drive unit, 17 . . . motor controller, 18 . . . light source, 21 . . . shifting guide, 22 . . . objective lens, 31 . . . data bus, 32 . . . CPU, 33 . . . main memory, 34 . . . external storage, 35 . . . transmission port, 36 . . . monitor, 37 . . . keyboard

BEST MODE FOR CARRYING OUT THE INVENTION

Figure 1:
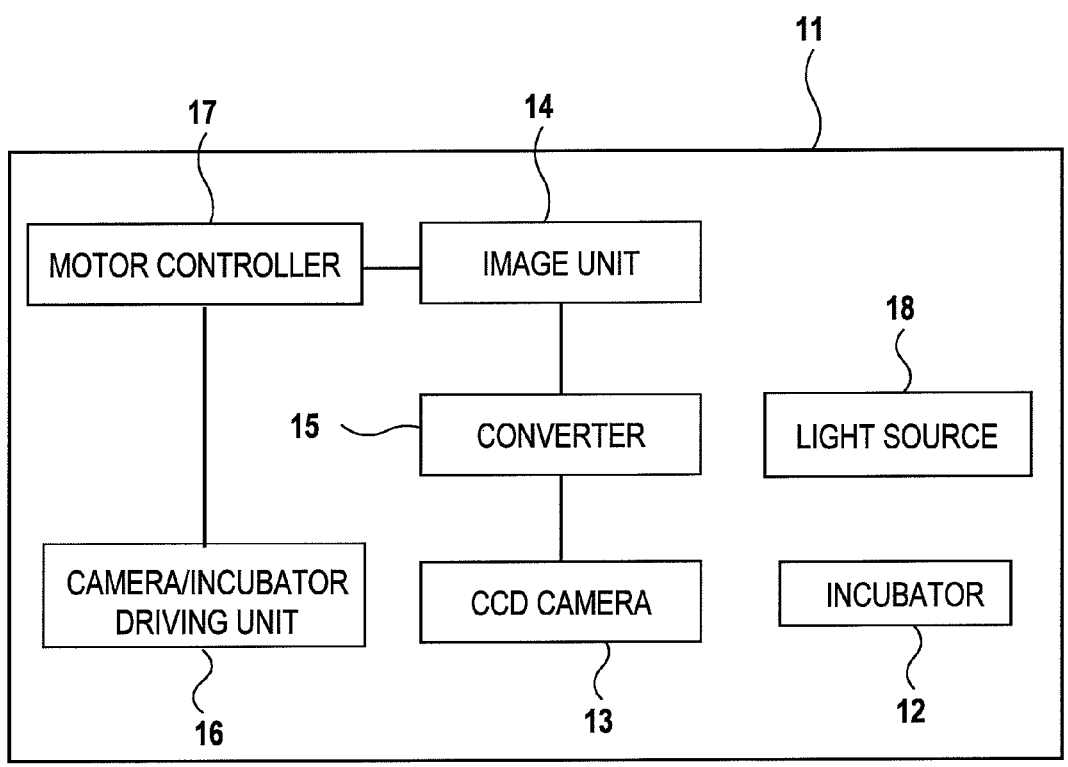
FIG. 1 is a block diagram showing the configuration of a cell culture device, image processing device and cell extracting system relating to the present embodiment.

Hereinafter, an embodiment of the present invention will be described based on the attached diagrams. FIG. 1 is a block diagram showing the configuration of a cell culture device, image-processing device and cell extracting system related to the present embodiment. As seen in the diagram, cell culture device 11 has a box structure which seals off the inside thereof from outer space, and contains therein:

incubator 12 for culturing cells;

CCD camera 13 for imaging the cells in incubator 12;

converter 15 for transferring image data obtained from CCD camera 13 to image-processing unit 14;

camera/incubator drive unit 16 for moving CCD camera 13 or incubator 12;

motor controller 17 for shifting camera/incubator drive unit 16 to an arbitrary position; and light source 18 mounted on the upper part of CCD camera 13. Incubator 12 has a transparent bottom surface, and CCD camera is configured to image transmitted light which is the light irradiated from light source 18 and transmitted through the bottom surface of incubator 12. In the above configuration, it is desirable that CCD camera 13 is provided with CCD device having about 400,000 pixels, and as for light source 18 it is preferable to use an LED or miniature bulb that emits not parallel light but diffusion light.

Figure 2:
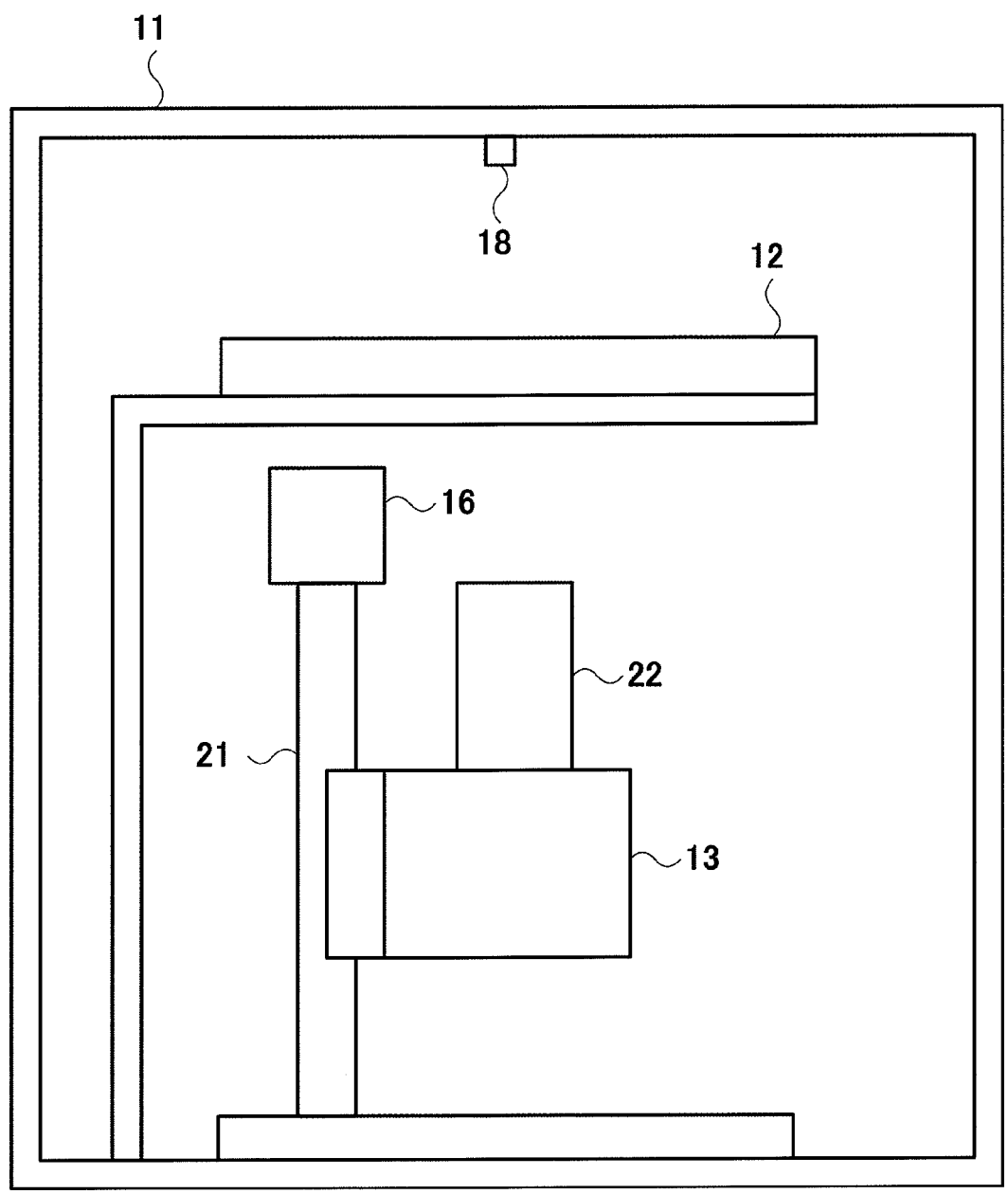
FIG. 2 is a diagram showing a schematic view of the arrangement of the respective configuration means in the cell culture device.

FIG. 2 is a schematic view of the arrangement of the respective configuration means in culture device 11, respectively illustrating the arrangement of incubator 12, camera/incubator drive unit 16, shifting guide 21 and objective lens 22 for the case of moving CCD camera 13 in culture device 11. As shown in the diagram, light source 18 is mounted on the top surface inside of culture device 11. Incubator 12 is placed under light source 18, and CCD camera 13 comprising objective lens 22 is placed under and near the center of incubator 12. CCD camera 13 carries out the imaging of the cells in incubator 12 by moving up and down according to the guidance of shifting guide 21 based on drive control of camera/incubator drive unit 16 operated by the command outputted from CPU 32, changing the focal point to upper and lower directions. In addition, it is desirable to configure an imaging device which is the combination of CCD camera 13 and objective lens 22 as capable of imaging minute areas, e.g. around 1.5 mm×2.0 mm, in the vicinity of the bottom surface positioned near the center of incubator 12.

Figure 3:
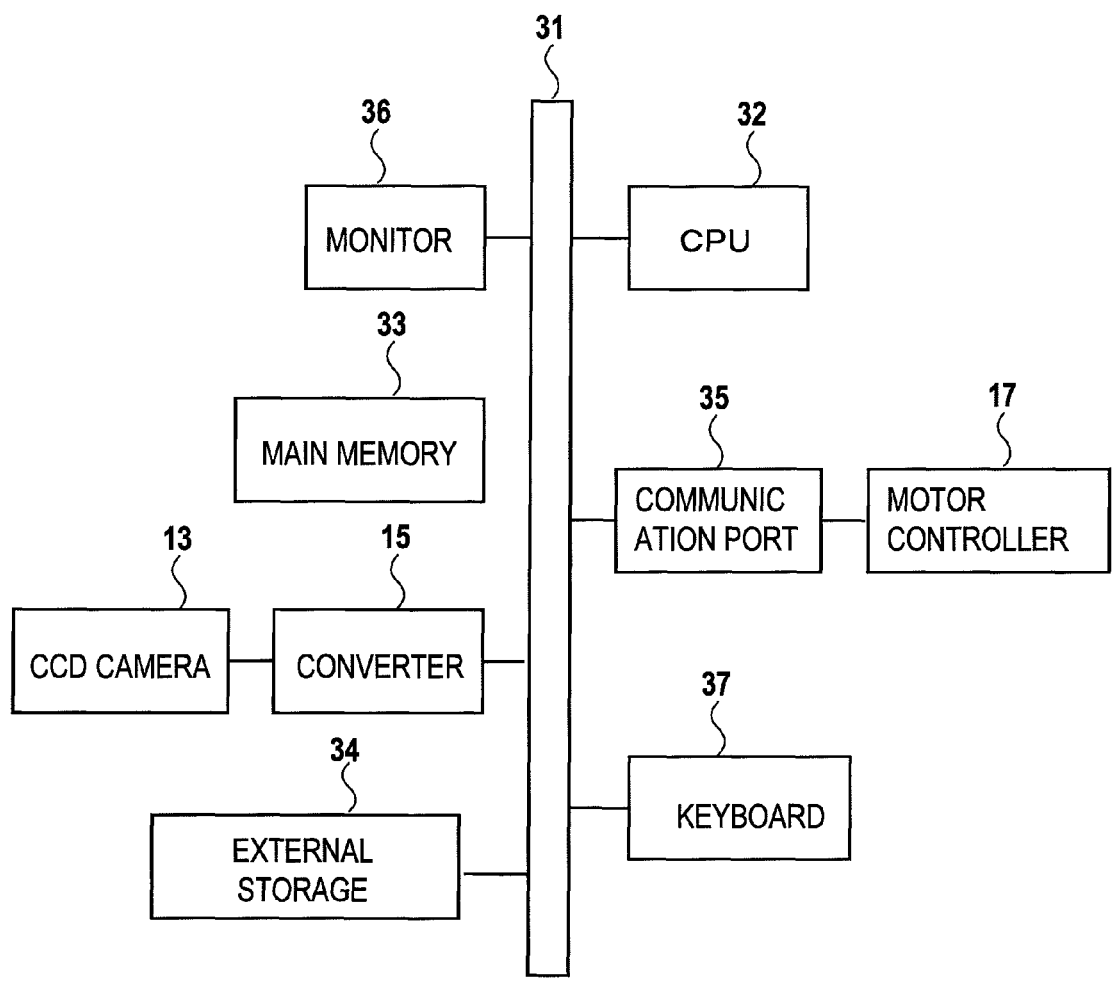
FIG. 3 is a diagram showing details of an image-processing unit in FIG. 1.

FIG. 3 is a diagram showing details of image-processing unit 14 in FIG. 1. Image-processing unit 14 comprises:

CPU 32 for performing calculation process via data bus 31;

main memory 33 for which CPU 32 temporarily uses as memory area;

external storage 34 for storing image data or positional information;

transmission port 35 for communicating with motor controller 17;

monitor 36 for displaying images after extracting the cells; and keyboard 37 for receiving the input by a user.

Figure 4:
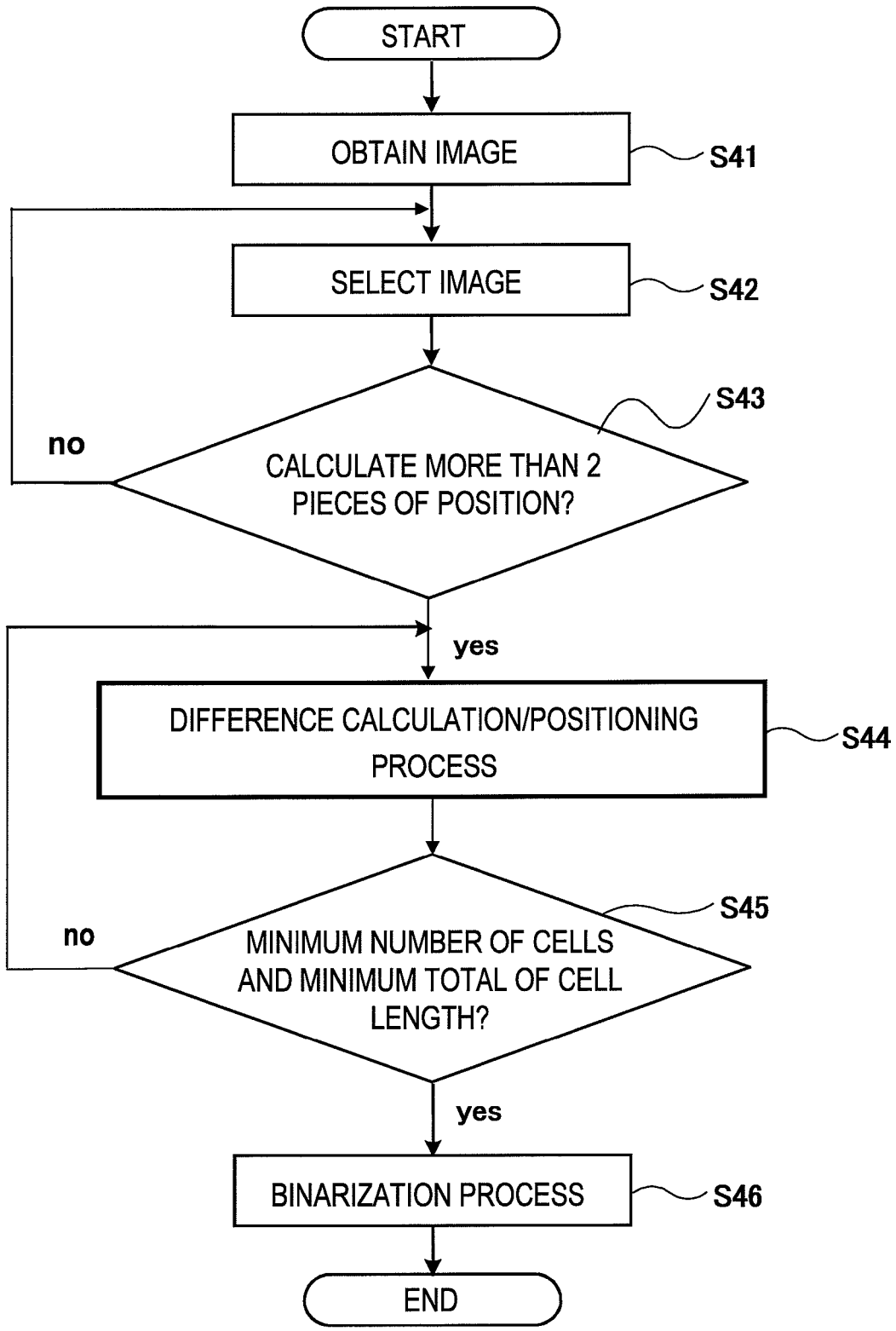
FIG. 4 is a flow chart showing an example of a cell extracting process by which the image-processing unit executes.

FIG. 4 is a flow chart showing an example of a cell-extracting process implemented by an image-processing unit. Steps for cell-extracting process shown in FIG. 4 will be described below.

A sequence of steps described in FIG. 4 is repeated at a frequency of, e.g. one time/day at predetermined time intervals in the process of cell culture, and is carried out by the unit described in FIGS. 1~3 being sequentially drive-controlled by the command outputted from the CPU. As for the timekeeper for repeatedly carrying out the sequence of steps described in FIG. 4 at predetermined time intervals, output of a clock generator provided in CPU 32 can be used.

(Step S41)

In step S41, images are acquired at predetermined pitch intervals, e.g. 27 μm intervals, while moving CCD camera 13 in up and down directions according to the command outputted from CPU 32 to motor controller 17. The plurality of image data acquired by this image-acquiring operation is stored in external storage 34 via converter 15.

(Step S42)

Figure 5:
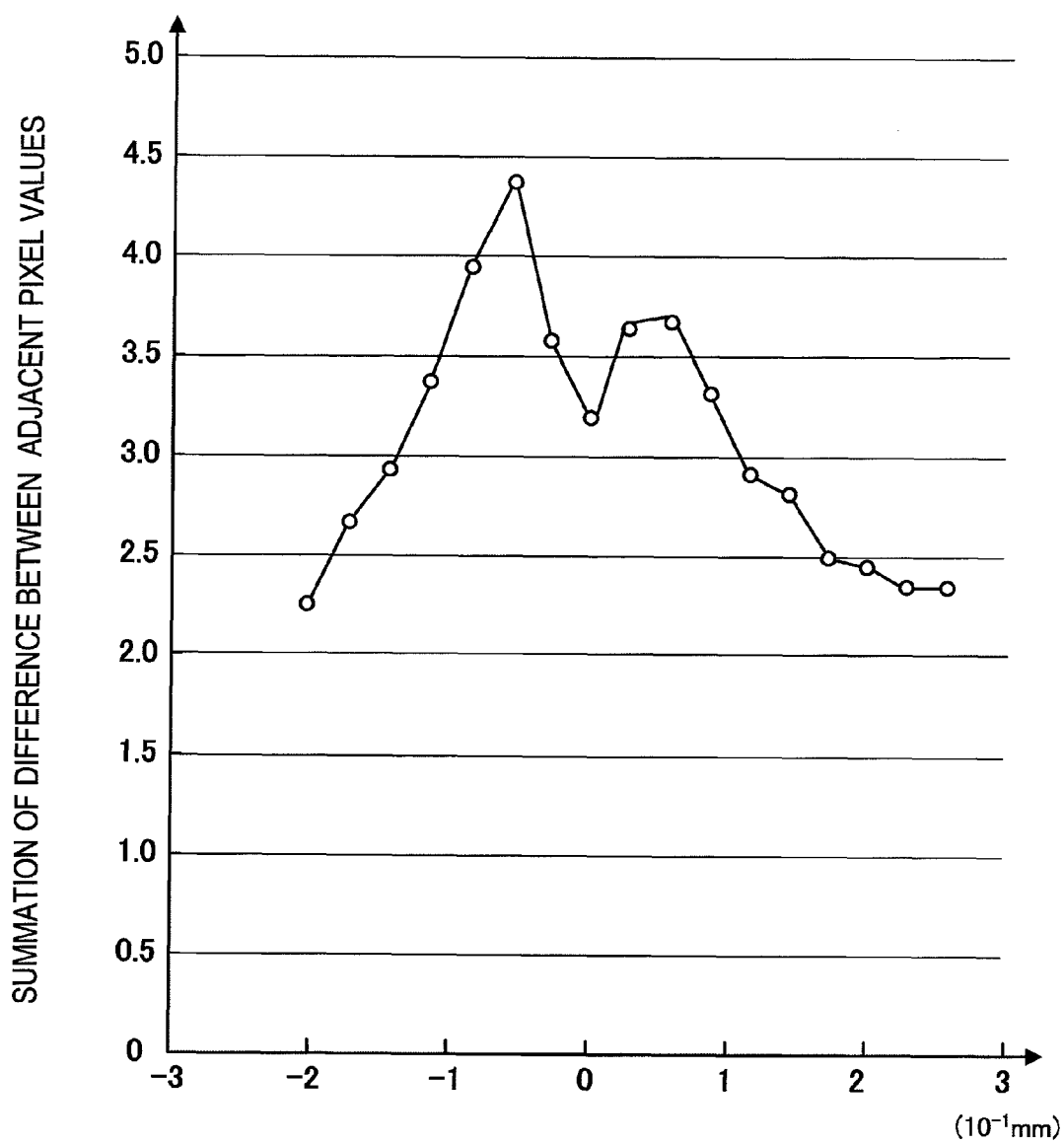
FIG. 5 is a diagram showing the relationship between shifting distance of a camera and summation of difference between adjacent pixel values.
Figure 6:
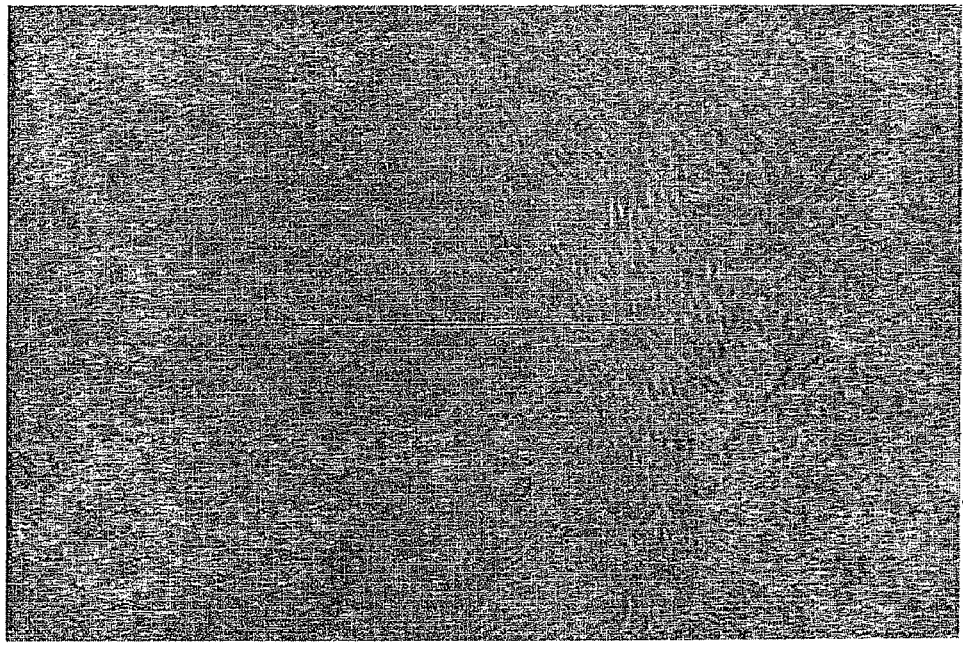
FIG. 6 is a diagram showing an example of an image when the focal point position of an objective lens is positioned on the bottom surface of an incubator.
Figure 7:
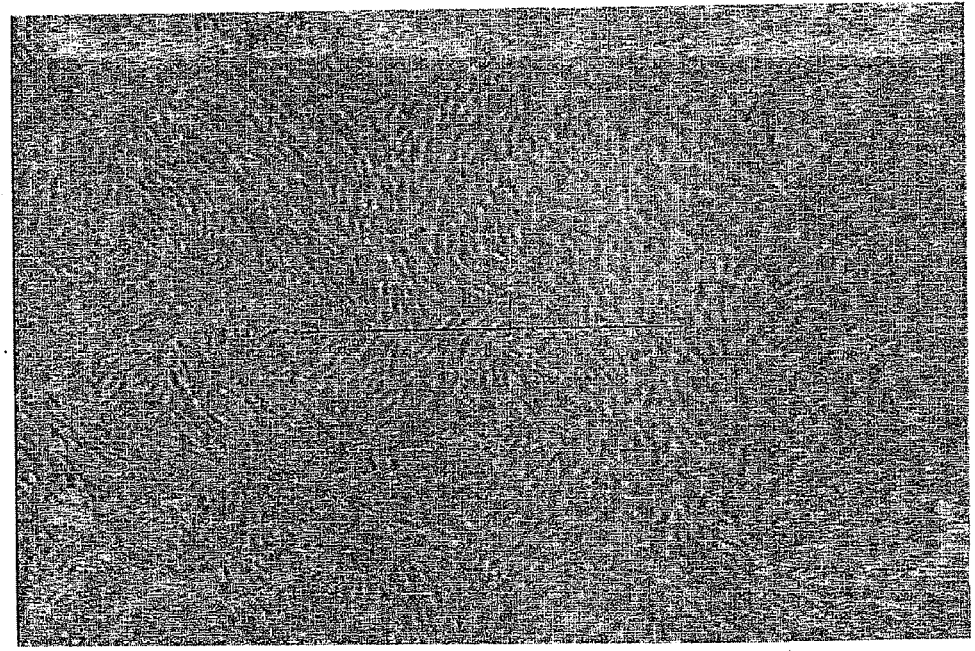
FIG. 7 is a diagram showing an example of an image when the focal point position of an objective lens is positioned in front (camera side) of the bottom surface of an incubator.
Figure 8:
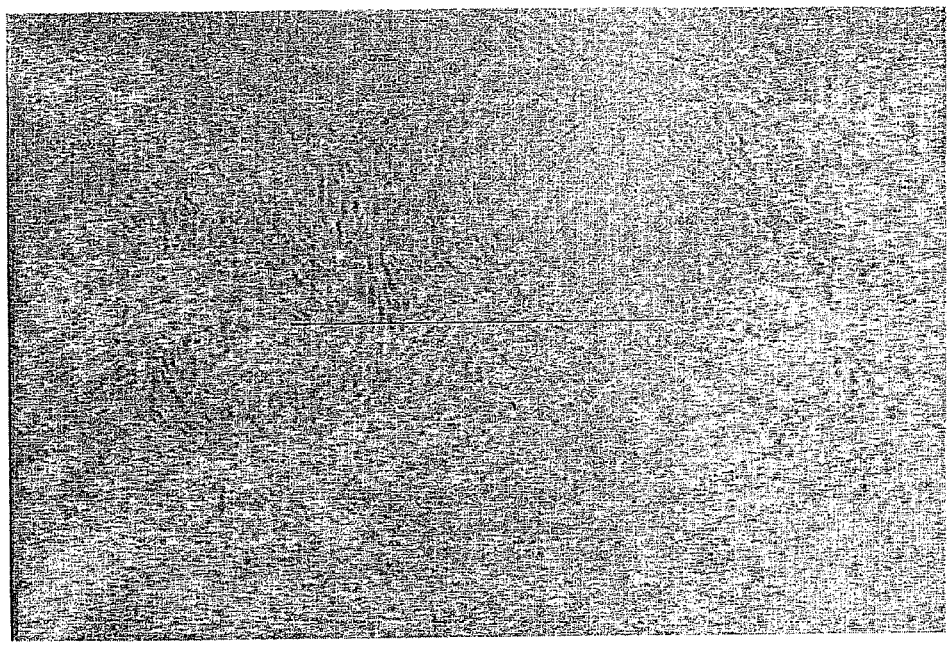
FIG. 8 is a diagram showing an example of an image when the focal point position of an objective lens is positioned in back (light source side) of an incubator.

In this step S42, image-selecting process is executed after obtaining all of the images. In this image-selecting process, two or more images of which the periphery of the cells is clear are selected from the plurality of images stored in external storage 34. In images having clear periphery of the cells, the changes in pixel values are greater compared to the images with unclear periphery of the cells. Given this factor, absolute values of the difference between adjacent pixel values is calculated, summation thereof is obtained and stored in main memory 33. FIG. 5 is a diagram showing relationship between shifting distance of the camera and summation of the difference between adjacent pixel values. There are two peaks shown in FIG. 5, and images indicating these peak values turn out as images having clear periphery of the cells. FIGS. 6~8 show the images at representative focal points of the camera in FIG. 5. Here, FIG. 6 is a diagram showing an example of an image in the case that the focal point position of objective lens 22 is positioned at the bottom surface of incubator 12, FIG. 7 is a diagram showing an example of an image in the case that the focal point position of objective lens 22 is positioned at the front side (camera side) of the bottom surface of incubator 12, and FIG. 8 is a diagram showing an example of an image in the case that the focal point position of objective lens 22 is positioned on the back side (light source side) of the bottom surface of incubator 12. These images are obtained by setting positions of the focal point shifting by very slight distance, thus intensity difference of these images is about the same. As is clear by the diagrams, it became evident from experimentation by the inventor that images having clearer periphery of the cells can be obtained when the focal point position of objective lens 22 is shifted either to the front or back of the bottom surface of incubator 12.

(Step S43)

In step S43, judgment whether more than two pieces of images comparable to the above-mentioned two peaks are selected or not, i.e. judgment of whether images having distinctive periphery of the cells shown in FIGS. 7 and 8 are obtained or not is made, when the answer is yes the next step S44 is carried out, and when the answer is no the step returns to step S42. In this image-selecting step, contour definition of the cell image is executed by carrying out image processing using profiling process, Fourier transformation or differentiation with respect to the images stored in the external storage 34. And the acquisition of the position of CCD camera 13 when it obtained an image having clear periphery of the cells is included in this step. The position of CCD camera 13 when it obtained the clear cell image is stored in the main memory 33 and is prepared for use upon the next cell-extracting process.

(Step S44)

In step S44, with respect to the two images selected in steps S42~S43, differential/positioning processing for coordinating the position of the cells in both images is carried out by setting a small image area of 256 pixels×256 pixels in the central portion of the images, and by calculating the difference between the small area of one image and the small area of the other image through shifting the images by 1 pixel each in X and Y directions. The reason for including the step for positioning of images in the embodiment is to take into consideration the possibility of some amount of displacement in the respective image positioning on the screen, though it depends somewhat on the degree of assembly accuracy of the device. Therefore, in a device free of displacement of image positioning while moving CCD camera 13, the step for image positioning can be omitted.

(Step S45)

The next judgment is made based on the result of differential/positioning processing of the previous step S44. That is, when the image of the cells displayed on the small image region is tilted heavily in longitudinal direction, judgment is made on whether the number of cells is minimum or not. The reason for this is because when the cells are in heavily tilted condition, if positioning is not accurate the cells are displayed being reduplicated and are observed as if many cells exist. Also, when the image of the cells displayed on the small image region is tilted heavily in lateral direction, judgment is made on whether the total length of the cells is minimum or not. The reason for this is because when the cells are ranged sideways, if positioning is not accurate the cells are observed as wider than the actual arrangement. As a result of the judgment, when the answer is yes the differential/positioning processing is ended at the position thereof and the step proceeds to step S46, and when answer is no the step returns back to step S44. Differential/positioning processing will be continued until judgment of step S45 comes out as yes. Here, when positioning of the two images is carried out by completion of differential/positioning processing, the cells are extracted on the difference image at that point. Though the reason for this is uncertain, the inventor assumes that it results from the two images having different focal point positions by which the cells received light being irradiated from a point source such as LED lamp, having information with different scattering state of light on surface of the cells. Also, as described in step S42, while images devoted for difference process has 19% density difference as shown in FIG. 5, influence by color variation of the medium, variation of the light volume, difference in brightness between the central and peripheral areas of the image and noise can be practically eliminated by calculating the difference.

(Step S46)

Figure 9:
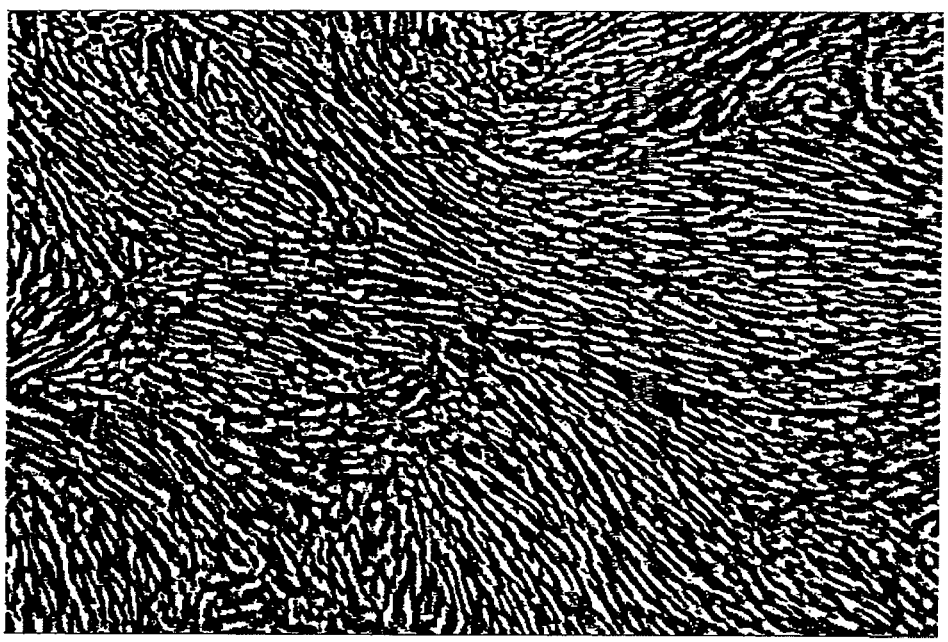
FIG. 9 is a diagram showing an image when differential/positioning processing and binarization processing is performed on images of FIGS. 7 and 8.

In step S46, in order to facilitate analysis of information of the cells such as their length, number or shape, a binarization process of images is carried out. FIG. 9 is a diagram showing an image as a result of implementing a binarization process with respect to the difference images having the minimum number of the cells and the minimum summation of the length of the cells, which is a result of the differential/positioning processing with respect to the images in FIGS. 7 and 8. In this way, by performing a binarization process on the difference images having the minimum number of the cells and the minimum summation of length of the cells thereof, individual cells are extracted clearly as white portions. The binarization process in step S46 is for facilitating data management thereafter by the computer, such as, e.g. counting the number of cells which will be described later, interval measurement between the cells and size measurement of the cells, and if these operations are not to be carried out step S46 can be omitted.

Analysis of information such as length, number and shape of the cells can be easily implemented based on the image in FIG. 9. More specifically, since the white portions in the binarization image of FIG. 9 represent the cells, reproduction rate of the cells can be estimated by counting the pixel number, and reproduction rate of the cells can also be estimated by measuring width of the black portions. Furthermore, by measuring length of the cells, growth rate of the cells can be estimated.

As described above, according to the present invention, since the cell culture device is configured comprising:

incubator 12 having a box structure which blocks off the inside thereof from outer space, and for culturing the cells therein;

CCD camera 13 for imaging the cells in incubator 12;

converter 15 for transferring image data obtained from CCD camera 13 to image-processing unit 14;

camera/incubator drive unit 16 for moving CCD camera 13 or incubator 12;

motor controller 17 for shifting camera/incubator drive unit 16 to an arbitrary position; and light source 18 mounted on the upper part of CCD camera 13, reproduction ratio of the cells can be observed without taking the cells in culture process out of the device. Also, since image analysis of the cells is regularly and automatically executed by the software installed in advance, labor involved in monitoring the cell culture can be reduced.

In the present invention, various changes may be made without departing from the scope of the invention. For example, in configuration of FIG. 1, images of the cells photographed by a camera or images on which the differential processing is performed can be displayed by connecting display for monitoring, e.g. liquid crystal display to image unit 14. Furthermore, size (length or radius) of the cells or distribution density of the cells in an incubator can be measured, and the measurement results can be displayed on the display for monitoring.

The invention claimed is:

1. A cell culture device provided with a storage container capable of forming a space sealed off from outer atmosphere, in which the following devices are disposed:
   an incubator for cell culturing;
   a light source for irradiating light to the cells in culture process in the incubator; and
   an image acquiring device for imaging the cells in culture process, placed in the back of the incubator with respect to the light source,
   as well as comprising means for processing images acquired by the image acquiring device and means for creating image data for extracting the cells,
   wherein the image data creating means comprises:
   means for selecting at least two images having clear periphery of the cells from the images acquired by changing the focal point positions;
   means for adjusting positions of the selected images; and
   means for carrying out the differential processing on the aligned images, and
   wherein the image acquiring device is disposed as movable in light source direction, and acquires the cell images of each focal point positions.

2. The cell culture device according to claim 1, wherein the image data creating means further comprises means for performing binarization processing on the image data implemented with differential processing.

3. The cell culture device according to claim 1, characterized in that the positioning/differential processing is carried out on the region smaller than the acquired images.

4. The cell culture device according to claim 1, comprising the means for automatically and repeatedly performing image acquisition, image analysis and creation of data for judging growth rate of the cells, at predetermined period of time intervals.

5. The cell culture device according to claim 1, characterized in comprising a display unit for displaying image data based on the images acquired by the image acquiring means.

6. A cell culture device comprising:
   incubator means for culturing cells;
   image acquiring means for acquiring images of the cells in the incubator means;
   focal point position adjusting means for moving either the image acquiring means or the incubator means, and adjusting the focal point of the image acquiring means to front and back of the cells in culture process in the incubator means;
   extracting means for extracting only the cell portions, with respect to the plurality of focal point positions set by the focal point position adjusting means, by carrying out differential processing on the plurality of image data having different focal point positions being acquired by the image acquiring means; and
   comprising focal point position calculating means for calculating the focal point position of the image acquiring means for acquiring most suitable images for extracting only the cell portions by the extracting means.

7. The cell culture device according to claim 6, further comprising position compensating means for compensating position of the plurality of image data acquired by the image acquiring means.

* * * * *